United States Patent [19]

Fassell et al.

[11] 3,953,502

[45] Apr. 27, 1976

[54] RECOVERY OF SILVER AND TEREPHTHALIC ACID COMPONENTS FROM LIGHT SENSITIVE FILM MATERIAL

[75] Inventors: W. Martin Fassell, Newport Beach, and Donald W. Bridges, Irvine, both of Calif.

[73] Assignee: Barber-Colman Company, Rockford, Ill.

[22] Filed: May 1, 1974

[21] Appl. No.: 466,015

[52] U.S. Cl............ 260/525; 260/515 P; 423/23; 423/35
[51] Int. Cl.².............. C07C 51/42; C01G 5/00
[58] Field of Search...... 260/525, 515 P, 475 D; 423/23, 35; 75/118 DIG. P

[56] References Cited
UNITED STATES PATENTS

| | | | |
|---|---|---|---|
| 3,544,622 | 12/1970 | England | 260/515 P |
| 3,020,312 | 2/1962 | Moscrip | 260/525 |
| 3,658,894 | 4/1972 | Juveland et al | 260/525 |
| 3,317,519 | 5/1967 | Lazarus et al | 260/239.3 |
| 2,131,072 | 9/1938 | Reid | 75/118 |

*Primary Examiner*— Anton H. Sutto
*Attorney, Agent, or Firm*— McDougall, Hersh & Scott

[57] ABSTRACT

The process for the recovery of silver and terephthalic acid component from scrap film of a light sensitive silver compound on a Mylar substrate in which the film is subjected to at least a partial wet oxidation in an aqueous alkaline medium at elevated temperature and pressure whereby the Mylar substrate is depolymerized into components which remain soluble in the liquid reactant while the silver component remains insoluble therein to enable separation of the silver component and the subsequent recovery of terephthalic acid component by acidification of the liquid phase.

16 Claims, 1 Drawing Figure

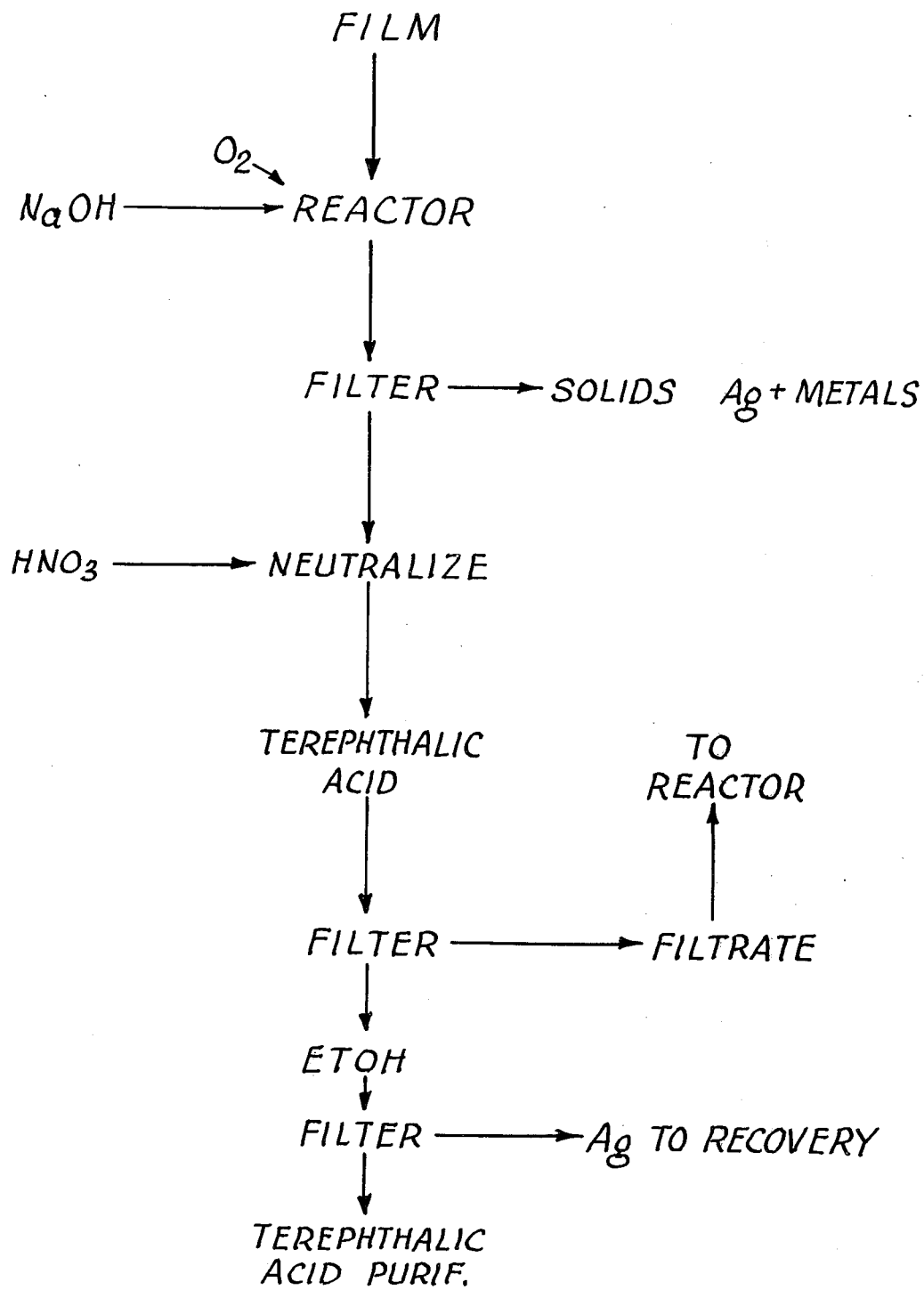

RECOVERY OF SILVER AND TEREPHTHALIC ACID COMPONENTS FROM LIGHT SENSITIVE FILM MATERIAL

This invention relates to the disposal of photographic or X-ray film and particularly to the disposal of exposed and unexposed photographic or X-ray film of the type formed of a silver halide emulsion coating on a base formed of Mylar (methyl terephthalic — ethylene glycol polyester), and still more particularly to the disposal of such material in a manner which enables substantially complete recovery of silver from the emulsion coating and the terephthalic acid component from the film base, and in which such disposal and recovery can be carried out in a pollution-free manner.

In our copending application filed concurrently herewith, and titled "The Process for the Destruction of Developed and Undeveloped Photosensitive Film and the Recovery of Products Therefrom", Serial No. 465,801, filed May 1, 1974, description is made of a process for the destruction of developed or undeveloped photosensitive film of silver halide emulsion on various organic substrates, by wet oxidation at elevated temperature and pressure, in aqueous medium containing a silver complexing component, such as an amine or ammonia, whereby the silver released from the coating on the substrate is converted to a soluble silver complex while the organic substrate material is consumed during the wet oxidation process or partially oxidized to usable organic components which can be recovered from the effluent of the wet oxidation reaction. The silver is separated from the solution by conversion of the silver from the soluble complex to an insoluble salt, such as by the addition of sulphuric acid to convert the silver complex to a separable insoluble silver sulphate; or by electrowinning the silver from the solution in which an acid, such as nitric acid, is added to enable plating out of the silver from the solution; or by reduction with hydrogen or other reducing agent to convert the silver from the soluble complex to metal solids which can be recovered by conventional solid-liquid separation techniques.

In the process described in the copending application, the formation of undesirable silver azides is possible and processing to maximize the recovery of silver requires treatment of the liquid phase, after silver separation, since some of the silver still remains in solution.

It is an object of this invention to provide a method for the processing of scrap light sensitive film, including exposed or unexposed light sensitive material, in which the recovery of silver is maximized, in which such recovery can be made in a simple and efficient manner with the expenditure of a minimum amount of time, materials, equipment and labor, in which when the film base is formed of Mylar or other terephthalate polyester, the terephthalic acid component can be recovered in good and economical yields, and wherein such recovery processes can be carried out without polluting the environment and with the elimination of scrap film as a potential pollutant.

In accordance with the practice of this invention, the Mylar based film, with the exposed or unexposed silver emulsion coating, is segmented as by cutting, chopping, beating, or other means of subdivision into relatively small particles which are then subjected to wet oxidation and preferably partial wet oxidation in an aqueous alkaline medium, with constant agitation, and at elevated temperature and pressure, for a time sufficient to effect cleavage of the polyester for separation of the terephthalic acid component. The breakdown of the polymer and the cleavage between the terephthalic acid component and the glycol of which the Mylar is formed is believed to result from a combination of hydrolysis and oxidation under the operating conditions existing within the reactor.

While wet oxidation beyond the minimum to achieve depolymerization and cleavage can be employed without jeopardizing the recovery of silver, it is desirable to minimize the amount of excessive oxidation if recovery of the terephthalic acid composition is an objective, since additional wet oxidation will result in additional combustion of the dissolved organic phase, with corresponding reduction in chemical oxygen demand (COD) of the solution and corresponding loss of terephthalic acid component.

Under the operating conditions described for complete and preferably partial oxidation of the organic film substrate, the undeveloped silver halide or the reduced silver in the exposed portion of the emulsion coating remains insoluble while the organic film base is reduced to a soluble state thereby to enable simple and efficient separation of the silver phase by conventional solid-liquid separation means, such as by filtration, centrifugal separation, decantation, and the like. The terephthalic acid component, dissolved in the liquid phase, after separation of the silver component, can be recovered by acidification of the alkaline solution whereupon the terephthalic acid component precipitates since it has very low solubility in aqueous acid medium (less than 0.02 grams per liter at 25°C).

Light sensitive silver halide coatings on film Mylar substrates represent a large segment of the market. X-ray film, often referred to in the trade as "medical green" is a major factor in the total film market and is almost entirely formed with a Mylar substrate. The photographic film market and the movie film market is increasingly making use of Mylar as the film substrate. Since terephthalic acid represents a valuable ingredient, currently in short supply, considerable interest is expressed in the recovery of terephthalic acid either as a principal product, or as a by-product, from the destruction of exposed or unexposed film and the recovery of silver therefrom.

The process of this invention will hereinafter be described by reference to the following examples 1 to 15, and the accompanying flow diagram. The examples are given by way of illustration and not by way of limitation of the invention.

The following is an identification of the various film materials that were processed in the examples:

| Film Code | General Description | Silver content, %w | Other |
|---|---|---|---|
| MG | Medical Green X-ray Film, unexposed | 3.6 | 6.5 moisture 86.2 volatiles 7.3 residue |
| BLC | Industrial lithographic film, non-Mylar base, exposed | 1.1 (clear) 2.7 (dark) | — |

| Film Code | General Description | Silver content, %w | Other |
|---|---|---|---|
| ITEK | Paper based film, exposed | – | – |
| VI | Black industrial X-ray film, exposed | – | – |
| TM | Tear medical, non-Mylar base, exposed | – | – |
| CP | Mixture of film from Naval Ordnance demonstration tests at Camp Pendleton, exposed | – | – |

EXAMPLES 1–15

The runs of Examples 1–15 were each carried out in an autoclave reactor having a capacity of one gallon and with the cylinder, baffle and stirrer formed of titanium.

In each example, the reactor was charged with 1470 ml of distilled water and the calculated amount of film and base material, and the stirrer was operated at 1000 r.p.m.

The autoclave was then closed and the specified amount of oxygen was added as pure oxygen. The temperature within the reactor was raised to a specified reaction temperature and the reaction was continued for a time, all as hereinafter set forth in the accompanying tabulation.

At the conclusion of the run, the reaction mixture was cooled rapidly by external water quench and the reactor was then opened. The cylinder was examined and the reaction product analyzed for the materials contained therein.

The effluent from the reactor was filtered to remove the insolubles which included the recoverable silver and silver halide components.

The filtrate was then acidified with nitric acid to precipitate the terephthalic acid component which was filtered off and then purified to remove entrained silver by resuspension in ethyl alcohol and filtering. Entrained silver remains with the filtrate while the purified terephthalic acid component separates as a solid.

Before each run, the reactor was thoroughly cleaned with a nitric acid rinse, followed by cleaning with a scouring powder. In Example 5, the reactor was further purged by pressurizing and depressurizing with nitrogen gas to eliminate any oxygen that might have been present.

In the examples, variations were made in the mean reaction temperature, reaction time, base material and film stock, as set forth in the following tabulation, to determine the effect of these variables on the recovery of silver, terephthalic acid component, and combustion of organic material. Examples 6 and 10 were atypical on account of low pH and other variables but were included for purposes of comparison.

All of the analyses recorded in the following tabulation were carried out in accordance with the procedures detailed in the EPA manual titled "Methods for Chemical Analysis of Water and Wastes – 1971".

The reaction mixture was measured for pH, chemical oxygen demand (COD), and for silver by atomic absorption. Cylinder liquid was tested for filterable solids on a No. 1 medium grade Whatman filter paper and terephthalic acid component (TPA). The latter involved acidification of the filtered liquid with nitric acid and subsequent gravimetric determination of the precipitate of terephthalic acid component removed on the filter. The percentage recovered TPA was based on the assumption that all of the non-moisture, volatile residues in the film were pure Mylar polyester. The ultimate or stoichiometric TPA content was calculated in accordance with the following equation:

$$30.0 \text{ grams film} \times 0.8625 \frac{\text{grms volatiles}}{\text{grm film}} \times \frac{1 \text{ grm polymer}}{1 \text{ grm volatiles}}$$

$$\times \frac{166 \text{ grms TPA}}{192 \text{ grms polymer}} = 22.37 \text{ grms. TPA}$$

The recovered terephthalic acid component was characterized by IR analysis. Two important evaluations were the COD and silver content in the final liquid effluent. As a basis for comparison, the theoretical total COD of effluent, using medical green film, is about 34,500 mg/1 0. The theoretical silver level in the final effluent would run between 900 and 1200 ppm if totally dissolved. For the purpose of this evaluation, no quantitative material balance was attempted on silver beyond showing its absence in the filtered liquid effluent. As the results discussed hereinafter indicate, the silver contents of the filtered effluents from all the tests were very low compared to the theoretical potential level of 1000 ppm. This is believed to establish that the silver was separated from the water soluble TPA salt.

TABLE 1

Summary of Process and Analytical Data from Film Hydrolysis Study

| | Principal Variables | | | | | Analytical Results | | | | | |
|---|---|---|---|---|---|---|---|---|---|---|---|
| Test No. | Mean Temp. °F | $O_2$ level mg | Ran Time, min | Base | Amt. Base (1) Stoich | Film | TPA (2) Recovery, % | Silver (3) in Filt. Liq. ppm | S.S. (4) in Liq. ppm | COD (5) mg/1 0 | % of COD (6) Due to TPA | Silver (7) in Digest FE, ppm |
| 1 | 464 | 30,160 | 130 | NaOH | 835 | Med. Gr. | 83.4 | 0.4 | 1006 | 21,733 | 84.1 | – |
| 2 | 400 | 31,020 | 130 | NaOH | 176 | Med. Gr. | 95.0 | 0.4 | 1352 | 28,450 | 73.4 | 1200 |
| 3 | 353 | 30,575 | 129 | NaOH | 176 | Med. Gr. | 99.1 | 2.8 | 876 | 31,962 | 67.5 | 350 |
| 4 | 349 | 660 | 124 | NaOH | 176 | Med. Gr. | 93.6 | 3.1 | 754 | 29,802 | 68.8 | – |
| 5 | 394 | <1 | 138 | NaOH | 176 | Med. Gr. | 67.5 | 0.4 | 1201 | 29,371 | 53.4 | – |
| 6 | 374 | 32,360 | 27.5 | NaOH | 176 | Med. Gr. | – | 1.3 | 4671 | 22,360 | – | – |
| 7 | 305 | 32,360 | 121 | NaOH | 176 | Med. Gr. | 12.2 (8) | 4.7 | 2276 | 15,881 | 17.0 | – |
| 8 | 397 | 32,360 | 129 | NaOH | 38 | Med. Gr. | 0.9 (9) | 0.1 | 4517 | 18,275 | 5.1 | – |
| 9 | 396 | 30,575 | 138 | NaOH | 76 | Med. Gr. | 52.7 | 0.1 | 5067 | 25,939 | 44.9 | – |
| 10 | 386 | 30,575 | 39 | NaOH | 176 | Med. Gr. | 89.2 | 2.6 | 172 | 29,288 | 66.1 | 450 |

Table I-continued

Summary of Process and Analytical Data from Film Hydrolysis Study

| Test No. | Principal Variables ||||||| Analytical Results |||||||
|---|---|---|---|---|---|---|---|---|---|---|---|---|
| | Mean Temp. °F | $O_2$ Level mg | Ran Time. min | Base | Amt. Base (1) Stoich | Film | TPA (2) Recovery, % | Silver (3) in Filt. Liq. ppm | S.S. (4) in Liq. ppm | COD (5) mg/l 0 | % of COD (6) Due to TPA | Silver (7) in Digest FE, ppm |
| 11 | 399 | 29,680 | 129 | KOH | 176 | Med. Gr. | 81.4 | 5.0 | 1084 | 28,106 | 62.8 | — |
| 12 | 390 | 31,020 | 145 | $Na_2CO_3$ | 176 | Med. Gr. | 94.2 | 0.3 | 573 | 28,697 | 71.9 | — |
| 13 | 399 | 31,915 | 125 | NaOH | 176 | BLC | — | 1.2 | 1452 | 20,985 | — | 390 |
| 14 | 396 | 32,360 | 130 | NaOH | 176 | Mixed (10) | 72 (6) (11) (12) | 1.7 | 1020 | 21,480 | 36.1 | — |
| 15 | 439 | 30,575 | 134 | NaOH | 176 | ITEK | — | 0.1 | 256 | 10,162 | — | — |

(1) Percentage of stoichiometric base required to form the sodium salt of terephthalic acid (TPA).
(2) Based on theoretical TPA content assuming non-moisture, volatiles are 100% Mylar.
(3) Silver dissolved in liquid at end of reaction.
(4) Suspended solids in cylinder liquid which are removed by simple filtration-normalized to account for pot volume.
(5) COD – normalized to account for pot volume and COD content.
(6) Percentage of COD due to recovered TPA.
(7) Silver in final effluent after solids were digested with acid.
(8) Also recovered unhydrolyzed film (32% of charge).
(9) Impure TPA: unhydrolyzed film remained.
(10) Mixture of 7.5 grams of each of the following: Black industrial, Camp Pendleton, tear medical and ITEK.
(11) Based on assumption that the Mylar based films – BI and CP – have similar Mylar content to that of med. green.
(12) Cellulose fibers remained.

The role of oxygen in the wet oxidation process is indicated by comparison of Examples 2, 4 and 5, wherein the oxygen level was varied from 31,020 mg in Example 2, to 660 in Example 4, and the complete absence of oxygen in Example 5. It will be seen that silver recovery, as indicated by the absence of silver in the filtrate, was equally low (0.4 ppm in the filtrate) with and without oxygen, indicating that the separation of silver from the film base was not oxygen dependent. On the other hand, the amount of terephthalic acid component recovered was considerably less in the absence of oxygen, indicating that at least partial oxidation in the alkaline wet oxidation process is beneficial to the cleavage of the polyester into its components.

The amount of oxygen introduced is therefore not significant by comparison of Examples 2 and 4 from the standpoint of the TPA recovery, but it is desirable to have oxygen present to provide for at least partial oxidation of the organics present in the system.

The oxygen can be added as pure oxygen, in the desired amount in a batch operation, but from a practical standpoint and for commercial practice wherein the recovery process can be carried out on a continuous or semi-continuous basis, it is desirable continuously to introduce the oxygen into the reaction medium, in the form of an oxygen containing gas such as pure oxygen, and preferably in the form of air. For this purpose, use can be made of a wet oxidation reactor, such as described in our copending applications Ser. No. 400,123 filed September 24, 1973, now U.S. Patent No. 3,870,631, and Ser. No. 403,652 filed October 4, 1973 now U.S. Patent No. 3,852,192.

By comparison of Examples 1, 2 and 3, it will be seen that the amount of combustion of organics in the reaction mixture is proportional to the reaction temperature, with but little actual reduction in COD occurring at a reaction temperature of 353°F (Example 3) or below, and with increasing reduction of COD at higher reaction temperatures such as the 400°F of Example 2 and 464°F of Example 1. Nevertheless, the amount of silver remaining in the reaction mixture after filtration is seen to be somewhat independent of the amount of oxidation under the conditions described.

Relatively low susceptibility of TPA to wet oxidation, by comparison with other organics in the liquor, is indicated by the lesser reduction in COD due to TPA by comparison with the entire system. This indicates that the terephthalic acid factor remains substantially high under the reaction conditions described to make it interesting to provide for commercial recovery of the TPA as well as the silver from scrap film.

From a comparison of Examples 1, 2, 3 and 7, it will be seen that recovery of TPA is at a maximum at a reaction temperature of about 350°F with little, if any, decrease in recoverable TPA up to 400°F. Thus it is desirable to make use of a reaction temperature of at least 350°F with the upper temperature limits being dictated more by economics and safety factors, since the autogenous pressures maintained within the reactor are temperature dependent. In the preferred practice of the invention, use is made of a reaction temperature within the range of 325°–425°F and preferably within the range of 350°–375°F, at corresponding autogenous pressure for a closed system.

Example 10 indicates that reaction time of 30 minutes is sufficient at reaction temperatures of 400°F and at a pH of 12.8 to 13.2. Longer reaction times are desirable at lower reaction temperatures, such as 60 minutes at 350°F, but within the preferred temperature range of 350°–375°F, a minimum of 10 minutes and a maximum of 180 minutes is employed, with the preferred reaction time being within the range of 30 to 60 minutes.

The amount of base in the reaction mixture, subjected to wet oxidation, bears considerable influence on the amount of TPA that is made recoverable by the process of this invention. This can best be expressed by the theoretical amount of base required to react with the TPA to neutralize the acid and from the corresponding metal salt thereof. The values given in the table are calculated on the stoichiometric amount as 100%. Thus the value of 38% in Example 8, and 76% in Example 9, indicates an amount corresponding to about ⅜ and ⅔, respectively, of the stoichiometric amount of base whereas the value of 176% indicates an excess of 76% over the stoichiometric amount. It will be apparent from a comparison of Examples 8 and 9 with Examples 1, 2 and 3, for instance, that with an amount of base less than stoichiometric, the recovery of TPA falls off considerably to practically zero recovery at 38% of the stoichiometric amount. The recovery of TPA drops only gradually above 200% of the stoichiometric but it is undesirable to make use of an amount of base in excess of 900% of the stoichiometric amount.

The amount of base can also be expressed from the standpoint of pH of the reaction mixture. For instance, at a pH of less than 9, the recovery of TPA is quite low. Best results are secured at a pH within the range of 10 to 14 and preferably within the range of 12 to 13.5.

As the base, it is preferred to make use of a strong base such as an alkali metal hydroxide or carbonate. As indicated by Examples 2, 11 and 12, it is preferred to make use of sodium hydroxide or sodium carbonate by comparison with potassium hydroxide, when measured from the standpoint of the silver which remains dissolved in the liquid filtrate after separation of the silver solids from the product of the wet oxidation reaction. 5 ppm silver remains in the filtrate formed with a base of potassium hydroxide, Example 11, whereas only 0.4 ppm and 0.3 ppm remains for sodium hydroxide, Example 2, or sodium carbonate, Example 12. Apparently the silver is more soluble in a potassium hydroxide solution than in a solution of sodium hydroxide or carbonate at equivalent pH.

Examples 13, 14 and 15 were runs made on film other than medical green. As indicated heretofore, Itek film is not formed with a Mylar substrate so that no TPA was recovered. Nevertheless, the recovery of silver was very high as indicated by less than 1 ppm of silver in the filtrate remaining after silver separation.

In Example 14, the film treated was made up of a mixture of Itek, Black Industrial X-ray film (BI), Tear Medical film (TM) and a mixture from Naval Ordnance (CP). All of the non-paper based films were hydrolyzed and the contained silver was precipitated. However, fibrous residues from the paper based Itek film were left behind. In Example 15, the Itek film was reacted at higher temperature (450°F) which brought about wet oxidation of the paper and thus eliminated solid organic residues. As with medical green, only trace silver was present in the effluent filtrated from these examples.

It will be apparent from the foregoing that we have provided a process for separation and recovery of silver and terephthalic acid from Mylar based photographic film. The film can be readily solubilized in aqueous alkaline solutions at temperatures above 300°F even in the absence of oxygen. If no oxygen is present, apparently about 33% of the TPA from the Mylar is tied up as acid-soluble species since only about 67% of the TPA is recovered upon acidification. In the presence of relatively small amounts of oxygen, essentially all of the TPA in the film is solubilized as free sodium terephthalate. The silver which remains insoluble is easily removed from the solubilized TPA in the product of the wet oxidation reaction.

If both TPA and silver are desired as products, the use of relatively low temperature with a small amount of oxygen represents the preferred practice. Under these conditions, TPA recovery is maximized while capital costs for equipment is maintained at a minimum. For special film types and for minimum COD discharge from the system, the process can be carried out at higher oxygen and temperature levels.

It will be understood that changes may be made in the details of formulation and operation without departing from the spirit of the invention, especially as defined in the following claims.

We claim:

1. A process for the treatment of a polyester formed of terephthalic acid for the recovery of terephthalic acid and silver when present therewith as a light sensitive compound comprising subjecting the polyester to at least partial wet oxidation at elevated pressure and a temperature of at least 325°F in an aqueous alkaline medium having a pH of at least 9 and into which an oxygen containing gas is introduced in an amount to provide at least partial oxidation of the organics present whereby any silver component present remains in the solid phase and the terephthalic acid component is contained in the liquid phase in a dissolved state, separating any solid phase from the liquid phase, acidifying the liquid phase to precipitate the terephthalic acid component, and then separating the terephthalic acid component from the remainder.

2. The process as claimed in claim 1 in which the wet oxidation reaction is carried out at a temperature within the range of 325°–425°F.

3. The process as claimed in claim 1 in which the wet oxidation reaction is carried out at a temperature within the range of 350°–375°F.

4. The process as claimed in claim 1 in which at least partial wet oxidation reaction is carried out for a time of at least 10 minutes.

5. The process as claimed in claim 1 in which at least partial wet oxidation reaction is carried out for a time within the range of 10 to 180 minutes.

6. The process as claimed in claim 1 in which at least partial wet oxidation reaction is carried out for a time within the range of 30 to 60 minutes.

7. The process as claimed in claim 1 in which the aqueous alkaline solution has a pH above 9.

8. The process as claimed in claim 1 in which the aqueous alkaline solution has a pH within the range of 12 to 13.5.

9. The process as claimed in claim 1 in which the aqueous alkaline solution is formed with a highly basic material present in an amount of at least 100% of the stoichiometric amount required to form the alkali metal salt of the terephthalic acid component.

10. The process as claimed in claim 1 in which the aqueous alkaline solution is formed with a highly basic material present in an amount within the range of 100% to 200% of the stoichiometric amount required to form the alkali metal salt of the terephthalic acid component.

11. The process as claimed in claim 9, in which the highly basic material is an alkali metal hydroxide or carbonate.

12. The process as claimed in claim 11 in which the basic material is selected from the group consisting of sodium carbonate and sodium hydroxide.

13. The process as claimed in claim 1 in which the liquid phase after separation of any insoluble silver component is acidified with nitric acid to precipitate the terephthalic acid component.

14. The process as claimed in claim 1 which includes the step of recovering the silver when present from the solid phase separated from the wet oxidation reaction product.

15. The process as claimed in claim 1 which includes the step of purifying the separated terephthalic acid component by treating the separated terephthalic acid component with an alcohol to dissolve out any silver retained with the terephthalic acid component.

16. A process for the treatment of scrap polyester formed of terephthalic acid for the recovery of terephthalic acid, comprising subjecting the polyester to at least partial wet oxidation in an aqueous alkaline medium at elevated pressure and at a temperature of at least 325°C and at a pH of at least 9 whereby the terephthalic acid component is contained in the dissolved state in the liquid phase, separating any solids from the liquid phase, acidifying the liquid phase to precipitate the terephthalic acid component, and then separating the terephthalic acid component from the remainder.

* * * * *